(12) United States Patent
Hirschberg et al.

US010723683B2

(10) Patent No.: US 10,723,683 B2
(45) Date of Patent: Jul. 28, 2020

(54) CONVERSION OF A PERFLUORINATED VINYL ETHER INTO A PARTIALLY FLUORINATED SATURATED ETHER DERIVATIVE

(71) Applicant: 3M INNOVATIVE PROPERTIES COMPANY, St. Paul, MN (US)

(72) Inventors: Markus E. Hirschberg, Burgkirchen (DE); Klaus Hintzer, Kastl (DE); Zai-Ming Qiu, Woodbury, MN (US); Gerd-Volker Röschenthaler, Bremen (DE); Romana Pajkert, Bremen (DE); Sergey N. Tverdomed, Bremen (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 16/065,502

(22) PCT Filed: Dec. 20, 2016

(86) PCT No.: PCT/US2016/067674
§ 371 (c)(1),
(2) Date: Jun. 22, 2018

(87) PCT Pub. No.: WO2017/112629
PCT Pub. Date: Jun. 29, 2017

(65) Prior Publication Data
US 2018/0370888 A1 Dec. 27, 2018

Related U.S. Application Data

(60) Provisional application No. 62/387,598, filed on Dec. 24, 2015.

(51) Int. Cl.
*C07C 41/30* (2006.01)
*C07C 249/02* (2006.01)
*C07C 253/18* (2006.01)
*C07C 41/18* (2006.01)
*C07C 43/12* (2006.01)
*C07C 251/08* (2006.01)
*C07C 255/13* (2006.01)

(52) U.S. Cl.
CPC .............. *C07C 41/30* (2013.01); *C07C 41/18* (2013.01); *C07C 249/02* (2013.01); *C07C 253/18* (2013.01)

(58) Field of Classification Search
CPC ....... C07C 41/18; C07C 41/24; C07C 249/02; C07C 253/18
See application file for complete search history.

(56) References Cited

U.S. PATENT DOCUMENTS 3,250,808 A 5/1966 Moore, Jr.
4,987,254 A 1/1991 Schwertfeger
5,260,492 A 11/1993 Feiring
8,440,858 B2 5/2013 Zipplies
2007/0142541 A1* 6/2007 Hintzer ................. C07C 59/135
524/544
2011/0245520 A1 10/2011 Zipplies

FOREIGN PATENT DOCUMENTS

JP          2008230981 A  * 10/2008  ............. C07C 41/06
JP          2009/521585 A    6/2009
WO      WO 1995-32174     11/1995
WO          2007/030314 A2   3/2007
WO      WO 2007-136948    11/2007
WO      WO 2009-042853     4/2009
WO      WO 2010-071730     6/2010
WO      WO 2011-050131     4/2011
WO      WO 2011-066156     6/2011
WO      WO 2017-112445     6/2017

OTHER PUBLICATIONS

Afsharpour, "Synthesis, characterization and catalytic activity of a new peroxomolybdenum(VI) complex-based coordination polymer", Applied Catalysis A: General, Aug. 2007, vol. 327, No. 2, pp. 205-210.
Czarnowski, "The 1,2-Fluorine Atom Migration in the Epoxide of 1,1 Dichlorodifluoroethene. The Infrared Spectrum of Dichlorofluoroacetyl Fluoride", Journal of Fluorine Chemistry, 1990, vol. 47, pp. 193-198.
Dlouha, "Reactivity study of 1,1,2,4,4,5,7,7,8,8,9,9,9-tridecafluoro-5-trifluoromethyl-3, 6-dioxanon-l-ene in nucleophilic reactions: fluorination properties of secondary amine adducts", Journal of Fluorine Chemistry, 2002, vol. 117, pp. 149-159, XP4389690A.
England, "Reactions of Amines with a Dimer of Hexafluoropropene and Perfluorovinyl Sulfide prepared with Hexafluoropropene", Journal of Fluorine Chemistry, Jun. 1981, vol. 17, pp. 265-288.
Feiring, "Fluorinated Vinyl Monomers", Organofluorine Chemistry: Principles and Commercial Application, (Edited by Bank et al.), 1994, pp. 341-342.
Furin, "Reaction of 1,1,2-trifluoro-2-hexafluoro-2'-(heptafluoropropoxy)-propoxyethylene with amines or alcohols", Journal of Fluorine Chemistry, 2000, vol. 106, pp. 13-24, XP55360491A.
Herbert, "Olefin epoxidations in the ionic liquid [$C_4$mim][$PF_6$] catalysed by oxodiperoxomolybdenum species in situ generated from molybdenum trioxide and urea-hydrogen peroxide: The synthesis and molecular structure of [Mo(O)($O_2$)$_2$(4-MepyO)$_2$]•$H_2$O", Polyhedron, Dec. 2009, vol. 28, No. 18, pp. 3929-3934.
Mimoun, "Vanadium(V) Peroxo Complexes. New Versatile Biomimetic Reagents for Epoxidation of Olefins and Hydroxylation of Alkanes amd Aromatic Hydrocarbons", Journal of the American Chemical Society, 1983, vol. 105, No. 10, pp. 3101-3110.

(Continued)

*Primary Examiner* — Rosalynd A Keys
(74) *Attorney, Agent, or Firm* — Thomas M. Spielbauer

(57) ABSTRACT

Methods of converting a fluorinated vinyl ether to a saturated partially fluorinated ether, the method comprising: reacting the fluorinated vinyl ether with an amine, ammonia, or combination thereof to form the saturated partially fluorinated ether.

21 Claims, No Drawings

(56) References Cited

OTHER PUBLICATIONS

Park, "Fluorinated C-Nitroso Compounds. II The Reaction of Nitric Oxide with Some Fluoroolefins in the Presence of Ferric Chloride", The Journal of Organic Chemistry, Sep. 1961, vol. 26, No. 9, pp. 3319-3323, XP55384824A.
Pola, "CW $CO_2$ Laser Driven Oxidation of Some Perhalogeno-Cycloalkenes", Collection of Czechoslovak Chemical Communications, 1991, vol. 56, pp. 398-405, XP55386729A.
Shipilov, "Selective Hydrolysis of Pentafluorobenzotrichloride", Russian Journal of Organic Chemistry, 2003, vol. 39, No. 7, pp. 975-978, XP2422334A.
Stockburger, "Reaction of Oxygen Atoms with 1,3-Perfluorobutadiene", Journal of the American Society, Jul. 1971, vol. 93, No. 14, pp. 3331-3336.
Toneli, "Photolysis of perfluoroacyl fluorides", Journal of Fluorine Chemistry, 2000, vol. 101, pp. 117-123, XP4244505A.
International Search Report for PCT International Application No. PCT/US2016/067674, dated Apr. 20, 2017, 5 pages.

\* cited by examiner

CONVERSION OF A PERFLUORINATED VINYL ETHER INTO A PARTIALLY FLUORINATED SATURATED ETHER DERIVATIVE

CROSS REFERENCE TO RELATED APPLICATIONS

This application is a national stage filing under 35 U.S.C. 371 of PCT/US2016/067674, filed Dec. 20, 2016, which claims the benefit of Provisional Application No. 62/387,598, filed Dec. 24, 2015, the disclosure of which is incorporated by reference in their entirety herein.

FIELD

The present disclosure relates to synthetic methods and compounds formed using such disclosed synthetic methods.

SUMMARY

Methods of converting a fluorinated vinyl ether to a saturated partially fluorinated ether, the method comprising: reacting the fluorinated vinyl ether with an amine, ammonia, or combination thereof to form the saturated partially fluorinated ether.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a conductive trace that "comprises" silver may be a conductive trace that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range. All upper and lower limits can be combined in any combination to form ranges for the particular component or property for example.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Use of "first," "second," etc. in the description above and the claims that follow is not intended to necessarily indicate that the enumerated number of steps are present. For example, a "second" step is merely intended to differentiate from another step (such as a "first" step). Use of "first," "second," etc. in the description above and the claims that follow is also not necessarily intended to indicate that one comes earlier in time than the other.

When a group is present more than once in a formula described herein, each group is "independently" selected, whether specifically stated or not. For example, when more than one $R^1$ group is present in a formula, each $R^1$ group is independently selected. Furthermore, subgroups contained within these groups are also independently selected.

As used herein, the term "room temperature" refers to a temperature of about 20° C. to about 25° C. or about 22° C. to about 25° C.

Prior methods of oxidizing fluorinated compounds utilized Lewis Acids, for example antimony pentafluoride and titanium chloride. Such methods provided low yields that are not workable for the production of usable quantities. Later methods added increased pressure, but still did not obtain desired yields. Other methods obtained higher yields, but utilized very large amounts of reagents and produced large amounts of undesirable byproducts. Therefore, there remains a need for additional methods of converting fluorinated compounds to chain reduced fluorinated compounds that may in some cases be more valuable.

Disclosed herein are methods of converting fluorinated compounds by ammonolyis into saturated partially fluorinated compounds or derivatives thereof. Ammonolysis can be described as a particular type of solvolysis reaction, which is a special type of nucleophilic substitution ($S_N1$) or elimination where the nucleophile is an ammonia molecule. Ammonolysis can produce simple protonated compounds, amines, other compounds or combinations thereof.

As used herein, "fluorinated" can refer to any compound that includes one or more than one fluorine (F) atoms bonded to a carbon. Fluorinated compounds can include partially fluorinated compounds and perfluorinated compounds. "Perfluorinated" means that all hydrogen atoms are replaced by fluorine atoms. For example, the term "perfluoromethyl" denotes an —$CF_3$ group. "partially fluorinated" means that at least one but not all hydrogen atoms are replaced by fluorine atoms. For example, a —$CFH_2$ group or a —$CF_2H$ group are examples of partially fluorinated methyl residues.

Compounds that can be converted herein can include any functionalities and can represent virtually any classes of compounds. In some embodiments, the fluorinated compounds can be described by the functionality(ies) that they may include, for example, the fluorinated compounds can include olefin compounds or olefin containing compounds, or ether containing compounds, for example. It should also be noted that a compound can be described by more than one class, for example a compound could be both an olefin containing compound and an ether containing compound. It should also be noted that fluorinated compounds to be converted herein can include any additional atoms, structures, or groups. Typically, the fluorinated compounds converted herein are fluorinated alkyl compounds that contain one or more than one functionality, such as those functionalities described herein.

As used herein "olefin containing compounds" or "olefin compounds" can refer to any compound that includes at least one carbon-carbon double bond. Olefin containing compounds can also be referred to as unsaturated compounds. Olefin containing compounds can include one or more than one carbon-carbon double bond.

As used herein "ether containing compounds" can refer to any compound that includes at least one oxygen atom interposed between two carbon atoms (R—O—R). Ether containing compounds can include one or more than one R—O—R group. In some embodiments, ether containing compounds could be vinyl ether containing compounds. As used herein, "vinyl ether" means a moiety in a compound having two carbon atoms bonded to each other by a carbon-carbon double bond, and at least one ether oxygen bonded to one of said double-bonded carbons atoms.

In some embodiments, fluorinated compounds to be converted herein can include fluorinated olefin compounds, for example. Such fluorinated olefin compounds can be linear, branched, cyclic or combinations thereof. A linear olefin is one that includes only a single chain of carbon (or other atoms), whereas a branched olefin is one that includes at least one pendant carbon group. In some embodiments, linear or branched fluorinated olefins can be converted herein. In some illustrative embodiments, the linear or branched fluorinated olefins can also include one or more ether groups. In some illustrative embodiments, the linear or branched fluorinated olefins can be perfluorinated linear or branched olefins.

In some specific illustrative embodiments, fluorinated linear olefin containing compounds can include from four (4) to twelve (12) carbon atoms, from four (4) to eight (8) carbon atoms, or from four (4) to six (6) carbon atoms. Specific illustrative examples of perfluorinated vinyl-containing compounds can include $C_3F_7$—O—[CF($CF_3$)—$CF_2$—O]$_x$—CF=$CF_2$ (with x=0 or 1), $CF_2$=CF—O—$CF_2$—$CF_2$—O—$CF_3$, $CF_3$—O—($CF_2$)$_3$—O—CF=$CF_2$, $CF_2$=CF—O—$CF_2$—$CF_2$—O—$CF_2$—O—$CF_3$, $CF_2$=CF—O—($CF_2$)$_x$—O—CF=$CF_2$ (with x=2 to 6) or similar compounds. Specific illustrative examples of partially fluorinated olefin containing compounds can include $HCF_2$—$CF_2$—$CF_2$—O—[CF($CF_3$)—$CF_2$—O]$_x$—CF=$CF_2$ (with x=0 or 1) and $CF_3$—$CH_2$—O—CF=$CF_2$.

In some specific illustrative embodiments, fluorinated branched olefin containing compounds can include from four (4) to twelve (12) carbon atoms, from four (4) to ten (10) carbon atoms, or from four (4) to eight (8) carbon atoms. Specific illustrative examples of fluorinated branched olefin containing compounds can include $C_3F_7OCF(CF_3)CF_2OCF$=$CF_2$ (PPVE-2) (1-[1-[difluoro[(1,2,2-trifluoroethenyl)oxy]methyl]-1,2,2,2-tetrafluoroethoxy]-1,1,2,2,3,3,3-heptafluoro propane) or similar compounds.

In some embodiments, fluorinated compounds to be converted herein can include fluorinated ether containing compounds. Fluorinated ether containing compounds can include one or more than one ether groups. In some embodiments, fluorinated ether containing compounds can include one ether groups, two ether groups, or more than two groups. Fluorinated ether containing compounds can also include one or more carbon-carbon double bonds (e.g., be an olefin containing compound as well), for example. In some specific examples, the fluorinated ether containing compound including one or more carbon-carbon double bonds could be a vinyl ether containing compound. In some embodiments, fluorinated ether containing compounds may be perfluorinated ether containing compounds, for example. More specifically, they could be perfluorinated ether olefin containing compounds, for example. Even more specifically, they could be perfluorinated vinyl ether containing compounds, for example. Specific illustrative examples of perfluorinated vinyl ether containing compounds can include $C_3F_7OCF(CF_3)CF_2OCF$=$CF_2$ (PPVE-2) or similar compounds. Even more specifically, they could be perfluorinated vinyl ether containing compounds that include a second ether group, for example.

Disclosed methods include reacting the fluorinated compound, for example a fluorinated vinyl ether containing compound, with an amine, ammonia, or combinations thereof to form a saturated partially fluorinated ether compound.

In some embodiments ammonia can be reacted with the fluorinated compound. Ammonia, $NH_3$, is a gas at room temperature conditions. In some embodiments, the ammonia can be utilized as a solution of $NH_3$ in water, or an aqueous solution of ammonia. The ammonia can be present in solution at amounts (by weight) of not less than 10%, not less than 20%, not less than 25%, or not less than 27%. The ammonia can be present in solution at amounts (by weight) of not greater than 40%, not greater than 35% or not greater than 32%. In some embodiments, an ammonia solution in water can be a solution that has from about 28% to about 30% ammonia by weight in water. Ammonia could also be utilized in an alcohol solution. Examples of possible alcohols can include, for example methanol, ethanol, propanol, butanol, or combinations thereof. The amounts of ammonia in an alcohol solution can be the same or similar to the amounts illustrated above for an aqueous solution.

In some embodiments amines can be reacted with the fluorinated compound. Amines have the formula $R^1NH_2$, where $R^1$ is a carbon containing group with one (1) to ten (10) carbons. In some specific illustrative embodiments, the amines may have the formula H—$(CH_2)_x$—$NH_2$ with x=1 to 10.

Amines can also include polyamines such as diamines and triamines. Diamines could also be described as having the $R^1NH_2$ formula but $R^1$ itself includes another $NH_2$ group. The general formula of a diamine is therefore $NH_2R^2NH_2$, where $R^2$ is a carbon containing group. Illustrative diamines can include those with two carbons (e.g., ethylene diamine ($H_2N(CH_2)_2NH_2$), three carbons (e.g., 1,2-diaminopropane ($H_2NCH_2CH(NH_2)CH_3$), or 1,3-diaminopropane ($H_2N(CH_2)_3NH_2$)), etc. Amines can be reacted with a fluorinated compound in water, alcohol, or a combination thereof.

The amount of ammonia, amine or combination thereof (referred to herein as "ammonia/amine" when considering molar ratios or amounts of moles) reacted with the fluorinated compound can also be described by the molar ratio of the ammonia/amine to the fluorinated compound. In some embodiments, the moles of ammonia/amine to the amount of moles of fluorinated compound can be not less than 1 moles to 1 moles (1:1), not less than 2 moles to 1 moles (2:1), not less than 4 moles to 1 moles (4:1), or not less than 5 moles to 1 moles (5:1). In some embodiment, the moles of ammonia/amine to the amount of moles of fluorinated compound can be not greater than 10 moles to 1 moles (10:1), not greater than 8 moles to 1 moles (8:1), not greater than 5 moles to 1 moles (5:1), or not greater than 4 moles to 1 moles (4:1).

The ammonia, amine or combinations thereof can be reacted in a solution that contains only water, only alcohol (one or more), only inert solvent(s), or a solution that contains water and one or more alcohols. Inert solvents can include non-reactive solvents such as inert fluorinated (either partially fluorinated or perfluorinated) solvents, supercritical liquids or gases, for example supercritical carbon dioxide ($scCO_2$), or other such solvents. A solution that contains one or more alcohols (and optionally water) can be referred to herein as an alcoholic solution. A solution that contains water (and optionally one or more alcohols) can be referred to as an aqueous solution.

Various reaction conditions can be controlled and/or modified when carrying out various disclosed methods. Examples of such reaction conditions can include, for example temperature and pressure. In some embodiments, methods can be carried out at a temperature less than room temperature, e.g., 0° C. or greater. In some embodiments, methods can be carried out under an increased temperature (e.g. not less than room temperature, about 25° C.), for example. In some embodiments, reacting a fluorinated compound with an amine, ammonia, or combinations thereof can be carried out at temperatures of not less than 25° C., not less than 50° C., not less than 100° C., or not less than 150° C., for example. In some embodiments, reacting a fluorinated compound with an amine, ammonia, or combinations thereof can be carried out at temperatures of not greater than 300° C., not greater than 250° C., not greater than 200° C., not greater than 50° C., or not greater than 45° C. In some embodiments, methods can be carried out under an increased pressure (e.g., greater than atmospheric temperature, about 1 bar), for example. In some embodiments, disclosed methods can be carried out at pressures not greater than 20 bar (e.g., ≤20 bar), or in some embodiments not greater than 5 bar (e.g., ≤5 bar). In some embodiments, disclosed methods can be carried out at pressures not less than 1 bar (e.g., ≥1 bar).

Disclosed methods can be carried out using known synthesis methods, processes, reaction vessels and other standard equipment. Disclosed methods can be carried out in a batch mode, in a continuous mode (e.g., a flow reactor), or a combination thereof.

Disclosed methods convert fluorinated compounds, such as fluorinated vinyl ether containing compounds into saturated partially fluorinated ether containing compounds. The specific partially fluorinated ether containing compounds produced can depend, at least in part on the specific ammonia or amine reactants utilized, the solution (e.g., aqueous, alcoholic, or combinations thereof) that the reaction takes place in, the reaction conditions, or any combination thereof.

In some embodiments, Scheme 1 below represents a specific example of a fluorinated compound and a specific partially fluorinated ether containing compound that could be produced using disclosed methods. The particular example illustrated by Scheme 1 includes use of ammonia in aqueous solution with an increased temperature. The reaction that is illustrated by Scheme 1 generally decreases the number of carbons in the carbon chain. More specifically, it can be described as converting a —$CF_2OCFCF_2$ group in the fluorinated vinyl ether into a hydrogen (H) in the saturated partially fluorinated ether. It should be noted that these reagents and conditions are offered merely as an example.

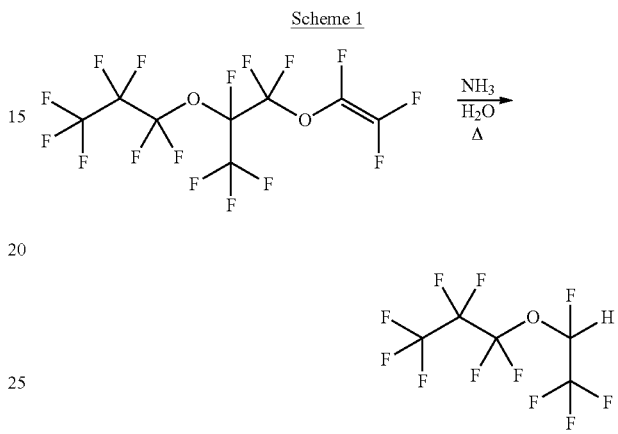

In some embodiments, Scheme 2 below represents a specific example of a fluorinated compound and a specific partially fluorinated ether containing compound that could be produced using disclosed methods. The particular example illustrated by Scheme 2 includes use of a diamine in aqueous solution with an increased temperature. It should be noted that these reagents and conditions are offered merely as an example.

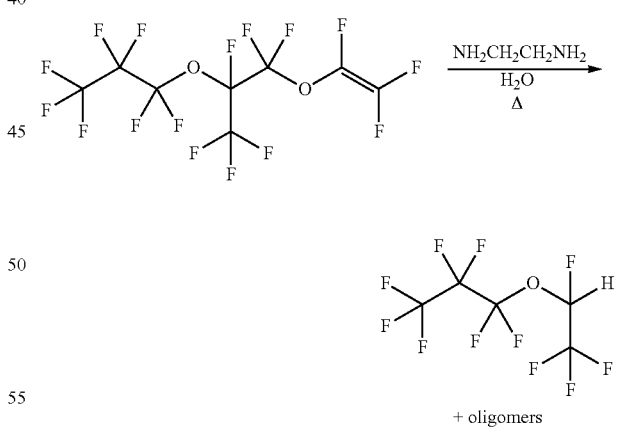

In some embodiments, Scheme 3 below represents a specific example of a fluorinated compound and a specific partially fluorinated ether containing compound that could be produced using disclosed methods. The particular example illustrated by Scheme 3 includes use of ammonia in an alcoholic solution. The reaction noted in Scheme 3 can be carried out at various temperatures, including for example from 0° C. to 45° C. It should be noted that these reagents and conditions are offered merely as an example.

Scheme 3

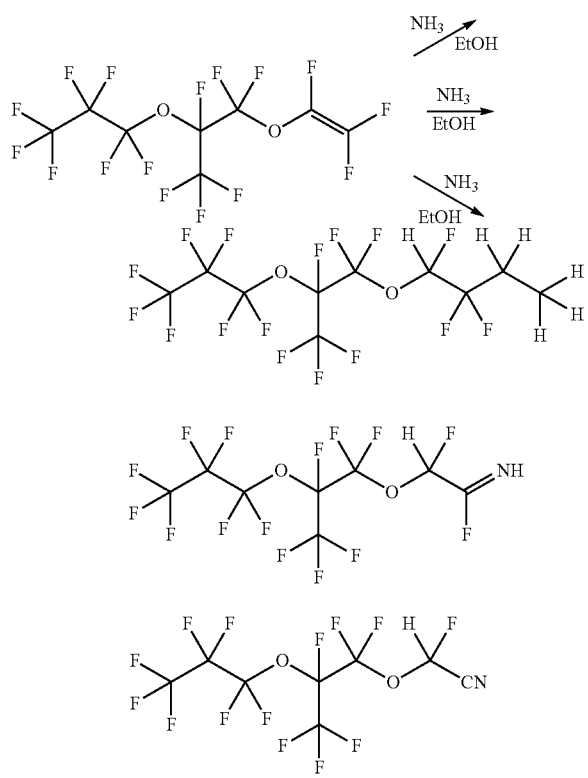

The following is a summary of particular, specific embodiments of the present disclosure.

Some illustrative embodiments include methods of converting a fluorinated vinyl ether to a saturated partially fluorinated ether, the method comprising: reacting the fluorinated vinyl ether with an amine, ammonia, or combination thereof to form the saturated partially fluorinated ether.

In the following paragraph "such methods" refer to the illustrative method immediately above as well as any other methods disclosed in this paragraph. Such methods, wherein the fluorinated vinyl ether comprises 1,1,1,2,2,3,3-heptafluoro-3-({1,1,1,2,3,3-hexafluoro-3-[(trifluoroethenyl)oxy]propan-2-yl}oxy)propane, which is also known as PPVE-2. Such methods, wherein the ammonia, amine or combination thereof is present in a molar ratio of from about 1:1 to about 10:1 of the moles of the fluorinated vinyl ether. Such methods, wherein the ammonia, diamine or combination thereof is present in a molar ratio of from about 4:1 to about 8:1 of the moles of the fluorinated vinyl ether. Such methods, wherein the reaction occurs at a temperature from about 0° C. to 250° C. Such methods, wherein the reaction occurs at a temperature from about 25° C. to 200° C. Such methods, wherein the reaction occurs at a temperature from about 50° C. to 200° C. Such methods, wherein the reaction takes place in an aqueous solution. Such methods, wherein the reaction takes place in a solution that contains water but no alcohol. Such methods, wherein the fluorinated vinyl ether is reacted with ammonia. Such methods, wherein the fluorinated vinyl ether is reacted with an amine. Such methods, wherein the fluorinated vinyl ether is reacted with a diamine. Such methods, wherein the saturated partially fluorinated ether has less carbons than the fluorinated vinyl ether. Such methods, wherein the fluorinated vinyl ether comprises a —$CF_2OCFCF_2$ group that is converted to a hydrogen (H) in the saturated partially fluorinated ether. Such methods, wherein the reaction occurs in an alcoholic solution. Such methods, wherein the reaction occurs in a solution that contains one or more alcohols but no water. Such methods, wherein the reaction takes place in a solution comprising methanol, ethanol, propanol, butanol, or combinations thereof. Such methods, wherein the ammonia, amine or combination thereof is present in a molar ratio of from about 1:1 to about 5:1 of the moles of the fluorinated vinyl ether. Such methods, wherein the ammonia, amine or combination thereof is present in a molar ratio of from about 2:1 to about 4:1 of the moles of the fluorinated vinyl ether. Such methods, wherein the reaction occurs at a temperature from about 0° C. to about 50° C. Such methods, wherein the reaction occurs at a temperature from about 20° C. to 45° C. Such methods, wherein the saturated partially fluorinated ether comprises $C_3F_7OCF(CF_3)CF_2OCFHCF_2C_2H_5$, $C_3F_7OCF(CF_3)CF_2OCFHCF=NH$, $C_3F_7OCF(CF_3)CF_2OCFHCN$, or combinations thereof.

Objects and advantages of this disclosure may be further illustrated by the following non-limiting examples, but the particular materials and amounts thereof recited in these examples, as well as other conditions and details should not be construed to limit this disclosure in any way.

EXAMPLES

Unless otherwise noted, all chemicals used in the examples can be obtained from Sigma-Aldrich Corp. (Saint Louis, Mo.).

The following abbreviations are used in this section: g=grams, mol=moles, mmol=millimoles, mL=milliliters, h=hours, NMR=nuclear magnetic resonance, MHz=megahertz, $T_{reaction}$=reaction temperature, $t_{reaction}$=reaction time, w/w=by weight.

TABLE 1

Materials used in examples

| Material | Description |
| --- | --- |
| PPVE-2 | Perfluoro(5-methyl-3,6-dioxanon-1-ene), available from abcr GmbH, Germany |
| Ammonia/Water | 28-30% aqueous solution of ammonium hydroxide, available from Sigma-Aldrich |
| Ethanol | Available from Sigma-Aldrich |
| Ethylene diamine | Availalble from Sigma-Aldrich, dissolved to 30% (w/w) in water |
| $Na_2SO_4$ | Available from Sigma-Aldrich |

Characterization

NMR spectra were obtained on a JEOL ECX 400 spectrometer operating at 400 MHz for $^1H$ (TMS), 376 MHz for $^{19}F$ ($CFCl_3$) and 100 MHz for $^{13}C$ (TMS) at 22° C. The yields were obtained by the weighed quantity of sample and the determined molar/weight ratio.

Example 1 (EX-1)

PPVE-2 (42.3 g, 0.1 mol) and a solution of ammonia/water (89.5 g of a 28-30% solution, 0.74 mol) were added to a steel autoclave (300 mL) equipped with a stir bar. The reaction mixture was heated upon intensive mixing at 160 to 165° C. for 12 h. After cooling to room temperature, the gaseous products were removed. The liquid residue of the autoclave (bottom layer) was separated and washed with water (3×25 mL) to neutral pH, dried over $Na_2SO_4$, and consisted of practically pure $C_3F_7$—O—CFH—$CF_3$. The yield of $C_3F_7$—O—CFH—$CF_3$ (molecular weight 286.0 g/mol) was 50% (15.3 g, 0.05 mol), confirmed by NMR.

Example 2 (EX-2)

The same procedure was followed as described for EX-1, with the following deviations: the amount of PPVE-2 used was (14.4 g, 33 mmol); instead of a solution of ammonia/water, a solution of ammonia in ethanol was used (39.3 g of a 2 M solution in ethanol, 0.1 mol); and the reactor was heated to 45° C. The procedure yielded a mixture of $C_3F_2OCF(CF_3)CF_2OCFH$—X, where X is $CF_2C_2H_5$, CF=NH, or CN, confirmed by NMR.

Example 3 (EX-3)

The same procedure was followed as described for EX-1, with the following deviations: the amount of PPVE-2 used was (29.1 g, 0.07 mol); and instead of a solution of ammonia/water, a solution of ethylene diamine in water was used (30% (w/w), 30.0 g (0.5 mol) of ethylene diamine in 105 mL water). The procedure yielded a mixture of $C_3F_7OCFHCF_3$ and oligomers, confirmed by NMR. The yield of $C_3F_7OCFHCF_3$ was 18%.

TABLE 2

| Example | Amine | molar ratio of amine:PPVE-2 | $T_{reaction}$ [° C.] | $t_{reaction}$ [h] | conversion of PPVE-2[a] | products |
|---|---|---|---|---|---|---|
| EX-1 | $NH_3/H_2O$ (30%) | 7:1 | 160-165[a] | 12 | 100 | $C_3F_7OCFHCF_3$ (isolated yield: 50%) |
| EX-2 | $NH_3$ in EtOH | 3:1 | 0-45 | 24 | 100 | mixture of $C_3F_7OCF(CF_3)CF_2OCFH$—X, where X is $CF_2C_2H_5$, CF=NH, or CN |
| EX-3 | $NH_2$—$(CH_2)_2$—$NH_2$/ $H_2O$ (30%) | 7:1 | 160-165[a] | 14 | 100 | $C_3F_7OCFHCF_3$ + oligomers (18% yield of $C_3F_7OCFHCF_3$) |

[a]autoclave condition

Thus, embodiments of methods for converting fluorinated compounds are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

Exemplary embodiments include the following:

Embodiment 1 fluorinated vinyl ether to a saturated partially fluorinated ether, the method comprising:
reacting the fluorinated vinyl ether with an amine, ammonia, or combination thereof to form the saturated partially fluorinated ether.

Embodiment 2

The method according to embodiment 1, wherein the fluorinated vinyl ether comprises 1,1,1,2,2,3,3-heptafluoro-3-({1,1,1,2,3,3-hexafluoro-3-[(trifluoroethenyl)oxy]propan-2-yl}oxy)propane.

Embodiment 3

The method according to any one of embodiments 1 or 2, wherein the ammonia, amine or combination thereof is present in a molar ratio of from about 1:1 to about 10:1 of the moles of the fluorinated vinyl ether.

Embodiment 4

The method according to any one of embodiments 1 to 3, wherein the ammonia, diamine or combination thereof is present in a molar ratio of from about 4:1 to about 8:1 of the moles of the fluorinated vinyl ether.

Embodiment 5

The method according to any one of embodiments 1 to 4, wherein the reaction occurs at a temperature from about 0° C. to 250° C.

Embodiment 6

The method according to any one of embodiments 1 to 5, wherein the reaction occurs at a temperature from about 25° C. to 200° C.

Embodiment 7

The method according to any one of embodiments 1 to 6, wherein the reaction occurs at a temperature from about 50° C. to 200° C.

Embodiment 8

The method according to any one of embodiments 1 to 7, wherein the reaction takes place in an aqueous solution.

Embodiment 9

The method according to any one of embodiments 1 to 7, wherein the reaction takes place in a solution that contains water but no alcohol.

Embodiment 10

The method according to any one of embodiments 1 to 9, wherein the fluorinated vinyl ether is reacted with ammonia.

Embodiment 11

The method according to any one of embodiments 1 to 10, wherein the fluorinated vinyl ether is reacted with an amine.

Embodiment 12

The method according to any one of embodiments 1 to 11, wherein the fluorinated vinyl ether is reacted with a diamine.

Embodiment 13

The method according to any one of embodiments 1 to 12, wherein the saturated partially fluorinated ether has less carbons than the fluorinated vinyl ether.

Embodiment 14

The method according to any one of embodiments 1 to 13, wherein the fluorinated vinyl ether comprises a —$CF_2OCFCF_2$ group that is converted to a hydrogen (H) in the saturated partially fluorinated ether.

Embodiment 15

The method according to any one of embodiments 1 to 14, wherein the reaction occurs in an alcoholic solution.

Embodiment 16

The method according to any one of embodiments 1 to 7 or 10 to 15, wherein the reaction occurs in a solution that contains one or more alcohols but no water.

Embodiment 17

The method according to embodiments 1 to 8 or 10 to 16, wherein the reaction takes place in a solution comprising methanol, ethanol, propanol, butanol, or combinations thereof.

Embodiment 18

The method according to any one of embodiments 15 to 17, wherein the ammonia, amine or combination thereof is present in a molar ratio of from about 1:1 to about 5:1 of the moles of the fluorinated vinyl ether.

Embodiment 19

The method according to any one of embodiments 15 to 18, wherein the ammonia, amine or combination thereof is present in a molar ratio of from about 2:1 to about 4:1 of the moles of the fluorinated vinyl ether.

Embodiment 20

The method according to any one of embodiments 15 to 19, wherein the reaction occurs at a temperature from about 0° C. to about 50° C.

Embodiment 21

The method according to any one of embodiments 15 to 20, wherein the reaction occurs at a temperature from about 20° C. to 45° C.

Embodiment 22

The method according to any one of embodiments 15 to 21, wherein the saturated partially fluorinated ether comprises $C_3F_7OCF(CF_3)CF_2OCFHCF_2C_2H_5$, $C_3F_7OCF(CF_3)CF_2OCFHCF=NH$, $C_3F_7OCF(CF_3)CF_2OCFHCN$, or combinations thereof.

The invention claimed is:

1. A method of converting a fluorinated vinyl ether to a saturated partially fluorinated ether, the method comprising:
reacting the fluorinated vinyl ether with an amine, ammonia, or combination thereof to form the saturated partially fluorinated ether wherein the saturated partially fluorinated ether has less carbons than the fluorinated vinyl ether,
wherein the reaction takes place in an aqueous solution.

2. The method according to claim 1, wherein the fluorinated vinyl ether comprises 1,1,1,2,2,3,3-heptafluoro-3-({1,1,2,3,3-hexafluoro-3-[(trifluoroethenyl)oxy]propan-2-yl}oxy)propane.

3. The method according to claim 1, wherein the ammonia, amine or combination thereof is present in a molar ratio of from about 1:1 to about 10:1 of the moles of the fluorinated vinyl ether.

4. The method according to claim 3, wherein the ammonia, amine or combination thereof is present in a molar ratio of from about 4:1 to about 8:1 of the moles of the fluorinated vinyl ether.

5. The method according to claim 1, wherein the reaction occurs at a temperature from about 0° C. to 250° C.

6. The method according to claim 5, wherein the reaction occurs at a temperature from about 25° C. to 200° C.

7. The method according to claim 6, wherein the reaction occurs at a temperature from about 50° C. to 200° C.

8. The method according to claim 1, wherein the reaction takes place in a solution that contains water but no alcohol.

9. The method according to claim 1, wherein the fluorinated vinyl ether is reacted with ammonia.

10. The method according to claim 1, wherein the fluorinated vinyl ether is reacted with an amine.

11. The method according to claim 1, wherein the fluorinated vinyl ether is reacted with a diamine.

12. The method according to claim 1, wherein the fluorinated vinyl ether comprises a —$CF_2OCFCF_2$ group that is converted to a hydrogen (H) in the saturated partially fluorinated ether.

13. A method of converting a fluorinated vinyl ether to a saturated partially fluorinated ether, the method comprising:
reacting the fluorinated vinyl ether with an amine, ammonia, or combination thereof to form the saturated partially fluorinated ether,
wherein the reaction occurs in an alcoholic solution.

14. The method according to claim 13, wherein the reaction occurs in a solution that contains one or more alcohols but no water.

15. The method according to claim 13, wherein the reaction takes place in a solution comprising methanol, ethanol, propanol, butanol, or combinations thereof.

16. The method according to claim 13, wherein the ammonia, amine or combination thereof is present in a molar ratio of from about 1:1 to about 5:1 of the moles of the fluorinated vinyl ether.

17. The method according to claim 16, wherein the ammonia, amine or combination thereof is present in a molar ratio of from about 2:1 to about 4:1 of the moles of the fluorinated vinyl ether.

18. The method according to claim 13, wherein the reaction occurs at a temperature from about 0° C. to about 50° C.

19. The method according to claim 18, wherein the reaction occurs at a temperature from about 20° C. to 45° C.

20. The method according to claim 13, wherein the saturated partially fluorinated ether comprises $C_3F_7OCF(CF_3)CF_2OCFHCF_2C_2H_5$, $C_3F_7OCF(CF_3)CF_2OCFHCF=NH$, $C_3F_7OCF(CF_3)CF_2OCFHCN$, or combinations thereof.

21. The method according to claim 13, wherein the fluorinated vinyl ether comprises 1,1,1,2,2,3,3-heptafluoro-3-({1,1,1,2,3,3-hexafluoro-3-[(trifluoroethenyl)oxy]propan-2-yl}oxy)propane.

* * * * *